United States Patent [19]
Boelart

[11] Patent Number: 5,896,169
[45] Date of Patent: Apr. 20, 1999

[54] VIDEO LEVEL MEASURING APPARATUS FOR X-RAY IMAGING SYSTEMS

[75] Inventor: Eduardo Irineo Boelart, Buena Park, Calif.

[73] Assignee: Philips Electronics North America Corporation, New York, N.Y.

[21] Appl. No.: 08/931,399

[22] Filed: Sep. 16, 1997

[51] Int. Cl.$^6$ .............................. H04N 17/00; H04N 5/57
[52] U.S. Cl. ........................... 348/181; 348/191; 348/687
[58] Field of Search ...................................... 348/180, 181, 348/184, 189, 191, 563, 576, 687

[56] References Cited

U.S. PATENT DOCUMENTS

| | | | |
|---|---|---|---|
| 3,567,854 | 3/1971 | Tschantz et al. | 348/687 X |
| 3,996,421 | 12/1976 | Pruznick et al. | 348/180 X |
| 4,855,830 | 8/1989 | Davis et al. | 348/687 X |
| 5,144,430 | 9/1992 | Boelart | 358/139 |
| 5,225,903 | 7/1993 | Wittrin | 348/687 X |
| 5,287,176 | 2/1994 | Stolle et al. | 348/687 X |
| 5,537,047 | 7/1996 | Boelart et al. | 324/613 |

*Primary Examiner*—Nathan Flynn
*Assistant Examiner*—John W. Miller
*Attorney, Agent, or Firm*—Dwight H. Renfrew, Jr.

[57] ABSTRACT

A video level measuring apparatus for use in conjunction with setup and maintenance of an imaging system, such as an X-ray imaging system, is configured for first and second modes of operation. In the first mode of operation, a measure signal indicative of the average video level of the portion of an input video signal produced by the imaging system within an operator positionable and sizable window area is formed and converted to a numeric displays and an augmented video signal is presented as an output video signal in which the window area of the corresponding image has a video level which is increased by a uniform adjustable amount. In the second mode of operations, a test pattern video signal corresponding to an operator positionable and sizable window of uniform operator adjustable brightness against a black background is presented as the output video signal applied to a monitor. The video level within the window area is measured and displayed on the numeric display and light measurements are made by the operator of areas on the screen of the monitor within the window area using a light meter. Both modes utilize the same window generation and video level measuring circuitry.

12 Claims, 1 Drawing Sheet

VIDEO LEVEL MEASURING APPARATUS FOR X-RAY IMAGING SYSTEMS

BACKGROUND OF THE INVENTION

1. Field of the Invention

The present invention relates to apparatus for measuring or analyzing a video signal within a positionable window area in a video image. Such an apparatus is particularly useful for measuring a video signal produced by a medical imaging system, for example, an X-ray imaging system.

2. Description of the Related Art

In commonly-owned U.S. Pat. No. 5,537,047, a device is disclosed for measuring noise content of a video signal, rather than its video level, within a positionable window area of fixed size in a video image produced by an X-ray imaging systems X-ray imaging systems of a type utilizing an X-ray image intensifier and camera chain to detect successive X-ray images and convert them to monochrome video images are being employed in a growing number of examinations. In addition to successive images which show the internal structure of an object under examination being available as a real time video display on a monitor, for example in fluoroscopy applications, the digitizing of these video images allows for digital image processing and/or archiving in a mass storage device. In order to set up such an imaging system and to periodically maintain or adjust its image quality, video levels (grey levels) and corresponding monitor light outputs are measured while one or more standard phantoms are employed as the objects under examination to determine whether the system's response characteristics are within standard levels. Measurement of video level may be done with an oscilloscope using a device such as described in commonly-owned U.S. Pat. No. 5,144,430, which generates a positionable marker in a video image and a corresponding oscilloscope trigger signal to allow a trace of the video line at which the marker is positioned to be displayed on the oscilloscope. Traces may be obtained and observed at various video lines corresponding to different X-ray attenuation levels in the phantom. Unfortunately, visual estimation of each pertinent video level from the oscilloscope trace is a subjective exercise which may vary between persons making the estimations and over the course of time. Further, in order to also determine the light image response of a monitor, light level is measured with a light meter at one or more predetermined places in the image of the phantom as it appears on the screen of the monitor. However, because the video level is somewhat irregular in the video supplied to the monitor by imaging a phantom, the light level measurements do not sufficiently isolate the video level to light output transfer function of the display alone.

SUMMARY OF THE INVENTION

It is an object of the present invention to provide a video measuring apparatus for producing a precise measure of video level in an operator positionable and sizable window area of a video image, which measure is preferably displayed as a numeric readout. It is a further object of the present invention that said analyzer be further configured for a mode utilizing the window generation and video measuring circuitry to generate a video test pattern having a measured constant video level within an operator positionable and sizable window area, for use in conjunction with monitor light output measurements.

Briefly, these and other objects of the present invention are satisfied by providing a video meter which produces a two-level gating signal which is at a predetermined level only during the times that the horizontal and vertical scanning signals that would be generated from the horizontal and vertical sync pulses correspond to a location within an operator positionable and sizable window area This gating signal and a selected video signal, which in a first mode of operation is the input video signal generated by the imaging device, are applied to a gated video signal averager which averages the video levels of the selected video signal present when the gating signal is at the predetermined level. The output signal of the gated video signal averager is digitized and used in driving a numeric display which indicates the measured average video level within the window area in the selected video signal. In this first mode of operation, an output video signal produced by the video meter constitutes the output signal from a combining circuit to which a window marking signal derived from the gating signal and the input video signal are applied. As a result, the output video image corresponds to the input video image, except in the window area, where the brightness or video level is increased by a constant value. This video output signal is supplied to the monitor of the imaging system so that the operator may observe the position and size of the window area superimposed on the image generated by the imaging system. The window marking signal is of the same form as the gating signal but has a brightness or video level in the window area which is adjustable by the operator.

The video signal fed to the gated signal averaging circuit is selected by a selector switch as either, for the first mode of operation, the input video signal supplied from the camera of the imaging system, or, for a second mode of operation, the output video signal produced by the analyzer which is produced solely by the window marking signal and represents an electronically generated test pattern consisting of a uniformly bright rectangular window area, of operator adjustable position, size, and video level, against a black background. Further, the adjustable video level is measured via the video measuring circuitry so that the value of the uniform video level in the window area is indicated on the numerical display. With the video meter being used in this mode, and the output video signal supplied to the monitor of the imaging system, the operator measures the light level at the monitor screen within the window area of the displayed test pattern with a light meter to determine, with the indicated video level, the video level to light level transfer characteristics of the monitor.

Other objects, features and advantages of the present invention will become apparent upon perusal of the following detailed description, when taken in conjunction with the appended drawing.

DETAILED DESCRIPTION OF THE PREFERRED EMBODIMENTS

Figure 1:
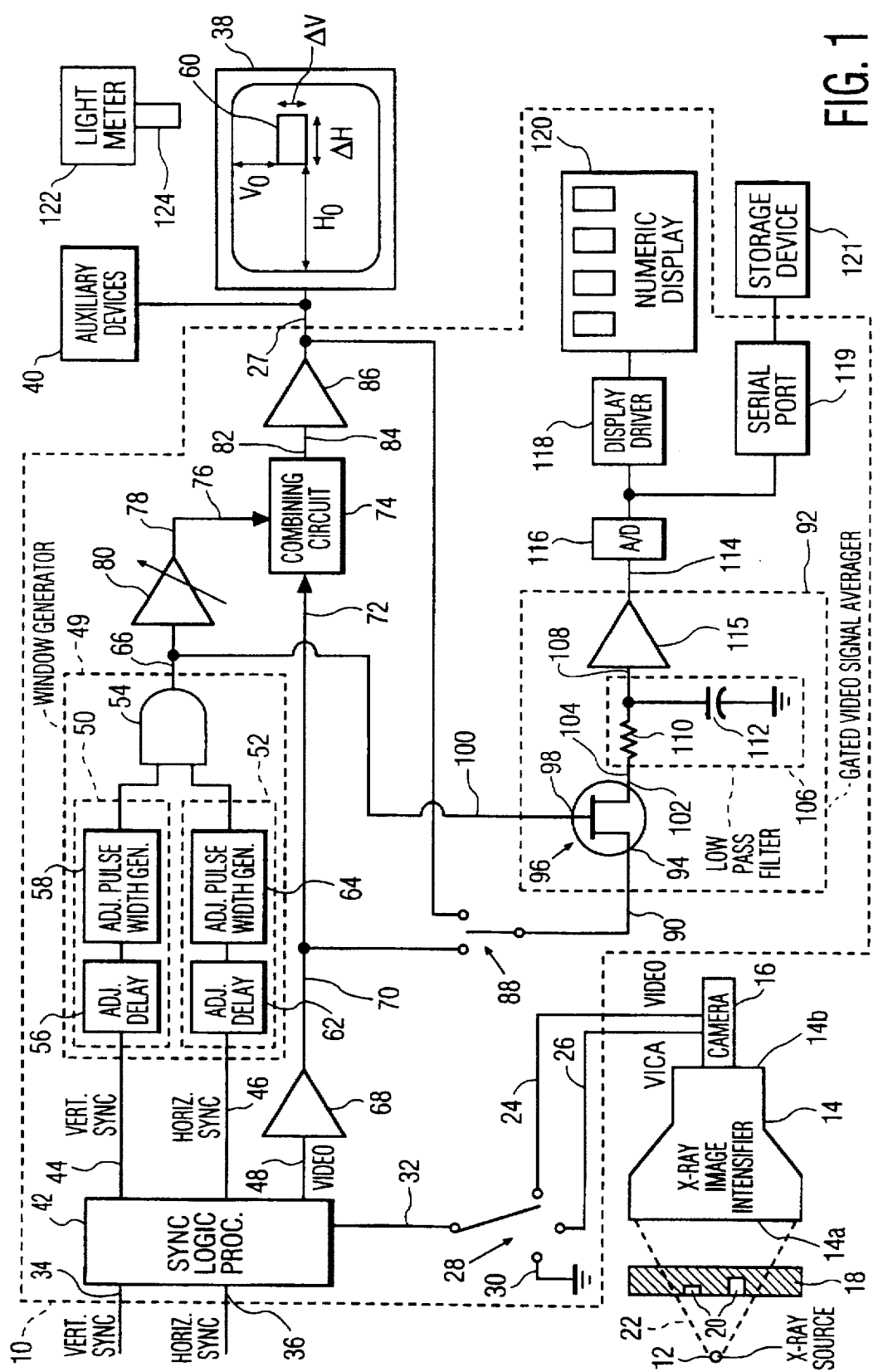
FIG. 1, the sole figure, is a schematic diagram of the video meter of the present invention in conjunction with an X-ray imaging systems

The video meter 10 of the present invention is generally shown in FIG. 1 in conjunction with an X-ray imaging system, including an X-ray source 12, X-ray image intensifier 14 and video camera 16, which system is set up for examination of a test phantom 18. The latter is preferably a copper plate having a general uniform thickness with different areas or steps 20 of reduced thickness constituting predetermined reduced X-ray attenuation characteristics.

A beam 22 of X-ray radiation from the X-ray source 12 is attenuated by test phantom 18 and forms an X-ray projection image on the front screen 14a of X-ray image intensifier 14 This X-ray image is converted by image intensifier 14 to an optical image on the output screen 14b. The camera 16 converts the optical image to a video image in the form of a video signal on its video output line 24 which is inputted to analyzer 10. This video signal is in standard form in that it includes the usual horizontal and vertical sync pulses. Further, it has a dynamic range which is set by automatic gain control (AGC) within the camera. Camera 16 also has a VICA output on line 26 which may also be inputted to analyzer 10 the VICA output has the same video content as presented on video output line 24 but without sync pulses and not affected by AGC. The video and VICA camera outputs on lines 24, 26 are fed to a selector switch 28 which connects a selected one of lines 24, 26, and a grounded or zero video line 30 to a video output 32 of switch 280 Further, the video analyzer has vertical and horizontal sync inputs 34, 36, respectively, for receiving sync signals from the imaging system. These signals are needed when VICA on line 24 or the zero video on line 30 is selected as the video output of switch 28, but are not necessarily needed when video in standard form is selected. Analyzer 10 produces an output video signal on its output line 27 which feeds a monitor 38 or other display device and auxiliary image or video receiving devices 40 such as for storage or recording and/or image processing.

The video signal from camera 16 may be the same format as in conventional television broadcasts in the United States, i.e. 60 fields per second which are 2:1 interlaced so that two successive fields, each containing 262.5 lines, in combination produce a 525 line frame. Other scan formats are common, including those which are non-interlaced, have a greater number of lines per frame, and/or have a greater number of frames per second. Such other formats, in general, have a faster horizontal line rate than conventional television in order to produce the requisite number of lines within a frame. Further, the X-ray source 12 may be operated in a pulse mode, triggered by vertical sync pulses supplied by camera 16 or in a "continuous" mode where a plurality of successive video frames are read out from camera 16 during a time interval that the X-ray source 12 is on.

Video meter 10 includes a sync logic processor 42 which receives vertical and horizontal sync signals on the analyzer's sync input lines 34, 36 and the video, VICA or zero video signal on the video output line 32 of selector switch 28 and produces vertical and horizontal sync signals on line 44, 46, respectively, and a video signal, including sync pulses, on line 48. When video in standard form is the selected switch output on line 32, and no sync signals are furnished to sync input lines 34, 36, the vertical and horizontal sync signals on lines 44, 46 are formed by extraction of sync pulses from the video signal. On the other hand, when VICA or zero video is the selected switch output on line 32, sync pulses derived from the sync signals on sync input lines 34, 36 are inserted to form the video signal on line 48.

A window generator circuit 49 comprises vertical and horizontal delayed pulse generators 50, 52 which are fed by the vertical and horizontal sync signals on lines 44, 46, respectively. The outputs of the vertical and horizontal delayed pulse generators 50, 52 feed an AND type circuit 54 which produces a two-level or binary gating signal on its output line 66 which is at a predetermined positive voltage level only during times when the pulses produced by the delayed pulse generators cause both inputs to the AND type circuit to be at the predetermined high level, and at other times is at a zero voltage level. Vertical delayed pulse generator 50 is formed by an adjustable delay element 56 followed by an adjustable pulse generator 58 which initiates a pulse of variable duration upon the expiration of a variable delay introduced by the delay element. Since the vertical sync pulse triggers each vertical scan in a downward direction beginning at the top of the image, the delay introduced by delay element 56 represents the distance $V_0$ from the top of the display to the top of window area 60. Further, the duration of the pulse produced by pulse generator 58 represents the vertical extent $\Delta V$ of window area 60. Similarly, the horizontal delayed pulse generator 52 is formed by the operator adjustable delay element 62 followed by operator adjustable pulse generator 64, the variable delay introduced by delay element 62 corresponding to the distance $H_0$ from the left side of the image to the left side of window area 32 and the variable duration of the pulse generated by pulse generator 64 corresponding to the horizontal extent $\Delta H$ of window area 60. It is well known how to construct variable delay elements and variable pulse width generators using analog elements such as one-shots having adjustable RC time constants. It should be apparent that the gating signal on line 66 produced by AND type circuit 54 is at the predetermined positive voltage level only when raster scanning signals derivable in monitor 38 in response to the vertical and horizontal sync pulses contained in the video signal on video output line 26 indicate an instantaneous position within both the vertical and horizontal extents $\Delta V$, $\Delta H$ of window area 60.

The respective delays or durations introduced by variable elements 56, 58, 62, and 64 are adjusted by respective control elements (not shown) which an operator may independently manipulate while observing the resultant vertical and horizontal position and vertical and horizontal size of the window area 60 on the display 38.

A buffer amplifier 68 receives at its input the video signal on output line 48 of sync logic processor 38 and the input video signal which appears at the output 70 of buffer amplifier 68 is fed to a first input 72 of a combining circuit 74. A second input 76 of combining circuit 74 is fed by a window marking signal which appears at the output 78 of a buffer amplifier 80 whose input is fed by the gating signal on window generator output line 66. Combining circuit 74 produces at its output 82 the sum of the input video signal and the window marking signal at its inputs 70, 72, respectively, and this output on line 78 feeds the input 84 of a buffer amplifier 86 whose output is the output video line 26 of analyzer 10. Amplifier 80 is adjustable in gain so that the operator may vary the brightness or video level of the widow marking signal within window 60, and thereby the value of a constant which is added to the video level of the input video signal within the window.

The input video and output video signals on lines 70, 27, respectively, are also fed to a selector switch 88 which passes a selected one of them to the video input 90 of a gated video signal averager 92. Within gated video averager 92, video input 90 is connected to an input signal terminal 94 of a transistor switch 96 and a control terminal 98 of the transistor switch is connected to a gate signal input 100 of the gated video signal averager. The gating signal on line 66 is fed to gate signal input 100 to control transistor switch 96 in a manner that the selected video signal is passed to the output signal terminal 102 of transistor switch 96 only during times when the input video signal corresponds to positions within the window area 60. The output signal terminal 102 of transistor switch 96 is connected to the input 104 of a low pass filter 106 having an output 108. Low pass filter 106 may be a simple RC circuit composed of a resistor 110 and capacitor 112. The time constant is chosen to be on the order of the reciprocal of the frame rate. The output 114 of gated signal averager, which is formed at the output of a buffer amplifier 115 whose input is fed by the output 108 of low pass filter 106, constitutes an analog signal which is a measure of the average of the video level within window area 60 of the video signal selected by selector switch 88. This measure signal on line 114 is supplied to an analog to digital converter 116. The output thereof feeds a numeric display driver 118 which in turn drives a numeric display 120, such as an LED display, which displays in numeric form a readout of the measured average video level. Further, an RS232 serial port 119 is fed from the output of analog to digital converter 116 in order to transmit the measured digital readings to an external storage device, such as a disk drive or memory (which may form part of a portable notebook or palmtop computer) for later reference. The automatic recording of measured video levels in this manner obviates the possibility of operator error in recording the readings by hand.

When the video meter 10 is used in a first mode of operation to measure average video level of the video or VICA signals 24, 26 as supplied by camera 16 and selected by switch 28, the selector switch 88 is set to feed input video from the output 70 of buffer amplifier 68 to the gated video signal averager 92. The output video signal of the analyzer on line 27 feeding monitor 38 constitutes an augmented video signal in which the window area 60 appears on the screen of monitor 38 as a rectangular area of increased brightness superposed on the input video signal. This superimposed window area is adjusted in size and position by the operator to fall within specific areas corresponding to selected attenuation steps 20 in phantom 18, and the average video level is read out on numeric display 120 for each step being measured.

In a second mode of operation used for monitor light output measurements, switch 28 is set to select zero video, so that the input video on line 70 supplied to combining circuit 74 contains only sync pulses. Further, the selector switch 88 is set to direct the output video on line 27 of video meter 10 to the input 90 of gated video signal averager 92. In this mode, the video signal on video output line 27 represents a test pattern in which window area 60 appears on the screen of the monitor 38 as a rectangle of constant video level against a black background, and a measure of this constant video level is shown on the numeric display 120. The operator adjusts the video level to a desired level by adjusting the gain of amplifier 80, and adjusts the size and position of the window area. Then, the operator measures the light output at selected locations on the screen of the monitor 38 using a light meter 122. If the light meter 122 has a small light receiving tip 124, such as ½ inch diameter in aperture, which is pressed against the screen of the monitor, window area may be large, because the area being measured is determined by the position and size of the tip. In applications where uniformity of the light output characteristics of the monitor is to be analyzed, it is possible to use a light meter which sees a large area of the screen and a small window area which is successively positioned to different locations It should now be appreciated that the objects of the present invention are fully satisfied by the apparatus described herein in particular detail. Numerous modifications in such detail are possible within the intended spirit and scope of the invention.

What is claimed is:

1. An video level measuring apparatus for receiving an input video signal generated by an imaging system and presenting an output video signal for driving a monitor, said apparatus comprising:

means for selecting either the input video signal or the output video signal as a selected video signal;

gating signal generating means responsive to scan control information associated with the selected video signal for generating a two-level gating signal which is at a predetermined level solely during the times that intensity information contained in said selected video signal corresponds to positions in a window area in an image corresponding to the output video signal;

measure signal forming means responsive to intensity information contained in said video signal and to said gating signal for forming a signal which is a measure of average video level solely within the window area of the image; and means for deriving and presenting in a first mode of operation an augmented video signal as the output video signal and in a second mode of operation a test pattern video signal as the output video signal, said augmented video signal being obtained by combining the input video signal and a window marking signal derived from the gating signal, and said test pattern signal being derived from said window marking signal.

2. The apparatus as claimed in claim 1, wherein said gating signal generating means further comprises adjusting means for enabling adjustment of the location and size of said window area in said image.

3. The apparatus as claimed in claim 1, wherein said measure signal forming means comprises an averaging means and switch means having a control electrode fed by said gating signal and a pair of main electrodes connected in a manner that said video signal is applied to said averaging means solely during the time the gating signal is at said predetermined level.

4. The apparatus as claimed in claim 2, wherein said measure signal forming means comprises an averaging means and switch means having a control electrode fed by said gating signal and a pair of main electrodes connected in a manner that said video signal is applied to said averaging means solely during the time the gating signal is at said predetermined level.

5. The apparatus as claimed in claim 2, wherein said scan control information comprises vertical sync pulses and horizontal sync pulses, and said adjusting means comprises:

first time delayed pulse generator means responsive to each vertical sync pulse for generating a first pulse of a first adjustable duration, corresponding to a vertical extent of said window area, a first adjustable time delay after said vertical sync pulse;

second time delayed pulse generator means responsive to each horizontal sync pulse for generating a second pulse of a first adjustable duration, corresponding to a horizontal extent of said window area, a second adjustable time delay after said horizontal sync pulse; and AND means, responsive to said first and second pulses for forming said gating signal.

6. The apparatus as claimed in claim 4, wherein said scan control information comprises vertical sync pulses and horizontal sync pulses, and said adjusting means comprises:

first time delayed pulse generator means responsive to each vertical sync pulse for generating a first pulse of a first adjustable duration, corresponding to a vertical extent of said window area, a first adjustable time delay after said vertical sync pulse;

second time delayed pulse generator means responsive to each horizontal sync pulse for generating a second pulse of a first adjustable duration, corresponding to a horizontal extent of said window area, a second adjustable time delay after said horizontal sync pulse; and AND means, responsive to said first and second pulses for forming said gating signal.

7. The apparatus as claimed in claim 1, wherein said window marking signal is derived from said gating signal in a manner that the video level of the window marking signal within the window area is adjustable.

8. The apparatus as claimed in claim 2, wherein said window marking signal is derived from said gating signal in a manner that the video level of the window marking signal within the window area is adjustable.

9. The apparatus as claimed in claim 3, wherein said window marking signal is derived from said gating signal in a manner that the video level of the window marking signal within the window area is adjustable.

10. The apparatus as claimed in claim 4, wherein said window marking signal is derived from said gating signal in a manner that the video level of the window marking signal within the window area is adjustable.

11. The apparatus as claimed in claim 5, wherein said window marking signal is derived from said gating signal in a manner that the video level of the window marking signal within the window area is adjustable.

12. The apparatus as claimed in claim 6, wherein said window marking signal is derived from said gating signal in a manner that the video level of the window marking signal within the window area is adjustable.

* * * * *